(12) United States Patent
Huang et al.

(10) Patent No.: US 12,033,734 B2
(45) Date of Patent: Jul. 9, 2024

(54) METHOD, DEVICE AND MEDIUM FOR STRUCTURING CAPSULE ENDOSCOPY REPORT TEXT

(71) Applicants: ANKON TECHNOLOGIES CO., LTD, Wuhan (CN); ANX IP HOLDING PTE. LTD., Singapore (SG)

(72) Inventors: Zhiwei Huang, Wuhan (CN); Wenjin Yuan, Wuhan (CN); Hao Zhang, Wuhan (CN); Hang Zhang, Wuhan (CN)

(73) Assignees: ANKON TECHNOLOGIES CO., LTD., Wuhan (CN); ANX IP HOLDING PTE. LTD., Singapore (SG)

( * ) Notice: Subject to any disclaimer, the term of this patent is extended or adjusted under 35 U.S.C. 154(b) by 887 days.

(21) Appl. No.: 17/112,971

(22) Filed: Dec. 4, 2020

(65) Prior Publication Data
US 2021/0174923 A1 Jun. 10, 2021

(30) Foreign Application Priority Data
Dec. 6, 2019 (CN) .......................... 201911241300.8

(51) Int. Cl.
*G16H 15/00* (2018.01)
*G06F 16/22* (2019.01)
(Continued)

(52) U.S. Cl.
CPC ......... *G16H 15/00* (2018.01); *G06F 16/2246* (2019.01); *G06F 40/205* (2020.01);
(Continued)

(58) Field of Classification Search
CPC ........ G16H 15/00; G16H 30/20; G16H 40/63; G06F 16/2246; G06F 40/205;
(Continued)

(56) References Cited

U.S. PATENT DOCUMENTS 10,755,804 B2 * 8/2020 Katwala ................ G06F 40/169
11,024,406 B2 * 6/2021 Sadeghi ................. G06Q 10/10
(Continued)

*Primary Examiner* — Cesar B Paula
*Assistant Examiner* — Zelalem Shalu
(74) *Attorney, Agent, or Firm* — Treasure IP Goup LLC

(57) ABSTRACT

The present invention discloses a method, device and medium for structuring a capsule endoscopy report text. The method includes: annotating the report text using an annotation model; storing each named entity classification label in the report text in a hierarchical tree structure according to the annotation information to form a tree structure diagram; parsing the tree structure diagram, extracting abnormal structure data and time parameters, and storing the abnormal structure data and time parameters in a panel data structured manner to form an abnormal structure panel table and a time parameter panel table. The present invention can automatically annotate the capsule endoscopy report through the annotation model, and output parameters of different amount of information in different structures, and quantitative and accurate quality control of the capsule endoscopy process and examination results, which provide sufficient convenience for the electronic medical information of the capsule endoscopy.

9 Claims, 8 Drawing Sheets

(51) Int. Cl.
*G06F 40/205* (2020.01)
*G06F 40/289* (2020.01)
*G06F 40/30* (2020.01)
*G06N 3/04* (2023.01)
*G06N 3/045* (2023.01)

(52) U.S. Cl.
CPC ............ *G06F 40/289* (2020.01); *G06F 40/30* (2020.01); *G06N 3/045* (2023.01)

(58) Field of Classification Search
CPC ...... G06F 40/289; G06F 40/30; G06F 16/258; G06F 16/35; G06F 16/367; G06N 3/045; G06N 3/042; G06N 3/044; G06N 3/047; G06N 5/01; G06N 5/046; G06N 7/01; G06N 5/022; G06N 3/08; Y02P 90/30
See application file for complete search history.

(56) References Cited

U.S. PATENT DOCUMENTS

2017/0242840 A1* 8/2017 Lu .................... G06F 40/169
2020/0334416 A1* 10/2020 Vianu ................ G06V 10/764

* cited by examiner

| Ga | s | t | r | i | c |   | f | u | n | d | u | s | : |   | t | h | e | r | e |   | i | s |   | a | n |   | u | l | c | e | r |   | a | b | o | u | t |   | 0 | . | 6 | c | m | , |   | w | i | t | h |
|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|
| B-OG | I-OG | I-OG | I-OG | I-OG | I-OG |  | I-OG | I-OG | I-OG | I-OG | I-OG | I-OG | I-OG |  | None | None | None | None | None |  | None | None |  | None | None |  | B-BX | I-BX | I-BX | I-BX | I-BX |  | B-YC3G | I-YC3G | I-YC3G | I-YC3G | I-YC3G |  | None | None | None | None | None | None |  | B-CLZ | I-CLZ | I-CLZ | I-CLZ | I-CLZ |

| h | y | p | e | r | e | m | i | a |   | a | n | d |   | e | d | e | m | a |   | i | n |   | t | h | e |   | s | u | r | r | o | u | n | d | i | n | g |   | m | u | c | o | s | a | . |
|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|
| B-YC3G | I-YC3G | I-YC3G | I-YC3G | I-YC3G | I-YC3G | I-YC3G | I-YC3G | I-YC3G |  | None | None | None |  | B-YC3G | I-YC3G | I-YC3G | I-YC3G | I-YC3G |  | None | None |  | None | None | None |  | B-SX | I-SX | I-SX | I-SX | I-SX | I-SX | I-SX | I-SX | I-SX | I-SX | I-SX |  | B-ZZ | I-ZZ | I-ZZ | I-ZZ | I-ZZ | I-ZZ | None |

FIG.5

```
"gastric area": {
    "gastric fundus": [
        {
            "gastric fundus##QG": {
                "mucus lake##ZZ": {
                    "clear##BX": {}
                },
                "varicose veins##YCJG": {
                    "no##FD": {}
                },
                "mucosa##ZZ": {
                    "smooth##BX": {}
                }
            }
        }
    ],
```

FIG.6

| Primary organs | Secondary organs | Abnormal structures | Size |
|---|---|---|---|
| stomach | gastric fundus | bumps | 0.4*0.3cm |
| | gastric angulus | hyperemia | |
| | gastric antrum | hyperemia | |
| | | erosion | |
| | pylorus | hyperemia edema | |
| duodenum | bulb | ulcers | |
| small intestine | jejunum | angiotelectasis | 0.3*0.5cm |
| | ileum | bumps | |
| large intestine | | tumors | |

FIG.7

| Primary organs | Entry time | Running time |
|---|---|---|
| esophagus | 2min23s | 59s |
| stomach | 3min22s | 19min12s |
| small intestine | 22min34s | 6h14min56s |
| large intestine | 6h37min30s | 3h38min50s |
| total running time | --- | 10h13min57s |

FIG.8

METHOD, DEVICE AND MEDIUM FOR STRUCTURING CAPSULE ENDOSCOPY REPORT TEXT

CROSS-REFERENCE OF RELATED APPLICATIONS

The application claims priority to Chinese Patent Application No. 201911241300.8 filed on Dec. 6, 2019, the contents of which are incorporated by reference herein.

FIELD OF INVENTION

The present invention relates to the field of medical device, and more particularly to a method, device and medium for structuring a capsule endoscopy report text.

BACKGROUND

Capsule endoscope is a medical device that integrates core components such as a camera and a wireless transmission antenna into a capsule that can be swallowed by a subject. During the examination, the capsule is swallowed into the body, and takes images in the digestive tract while transmits the images to the outside of the body, so as to perform medical examination based on the obtained image data.

Once the capsule endoscopy is completed, an examination report is generated, including examination findings, diagnosis results, and recommendations. Due to the different habits and writing styles of each doctor, each examination report is different. In addition, there are few doctors in the digestive tract, and the workload of them is heavy, omissions and mistakes may be caused in the report. In order to facilitate subsequent review and analysis, it is usually necessary to organize and annotate the report.

In the prior art, manual annotation is usually used to organize examination reports, which wastes manpower and increases the cost of annotation. In addition, the annotated report text still maintains the arrangement of the original text, which occupies a large amount of storage space and is not conducive to the query of the report.

SUMMARY OF THE INVENTION

In order to solve the above technical problems, the purpose of the present invention is to provide a method, device and medium for structuring a capsule endoscopy report text.

In order to achieve one of the above-mentioned objects of the invention, an embodiment of the present invention provides a method for structuring a capsule endoscopy report text, the method comprising: step S1, annotating the report text using an annotation model;

step S2, storing each named entity classification label in the report text in a hierarchical tree structure according to the annotation information to form a tree structure diagram, wherein the annotation information refers to the named category of each named entity classification label in the corresponding report text;

step S3, parsing the tree structure diagram, extracting abnormal structure data and time parameters, and storing the abnormal structure data and time parameters in a panel data structured manner to form an abnormal structure panel table and a time parameter panel table.

In an embodiment of the present invention, the method further comprises: step S4, selectively outputting at least one of the tree structure diagrams, the abnormal structure panel table, and the time parameter panel table.

In an embodiment of the present invention, the method for obtaining the annotation model in step S1 specifically comprises:

step M1, constructing a small neural network model using the BiLSTM+CRF structure and constructing a large neural network model using the BERT structure, wherein the initial small model and the large model have the same named entity division rules, and pre-annotating a current set of report texts using the small model and the large model, respectively;

step M2, reviewing and correcting the current report text annotated by the large model to form a revised report text;

step M3, verifying the small model with the revised report text, and obtaining the log-likelihood loss function corresponding to the small model;

step M4, revising the named entity division rules corresponding to the small model with the currently obtained revised report text and training the small model, and using the trained small model as an annotation model, when the log-likelihood loss function is not greater than the preset first function value; proceeding to step M5, when the log-likelihood loss function is greater than the preset first function value;

step M5, revising the named entity division rules corresponding to the small model and the large model with the currently obtained revised report text, and training the large model and the small model, and pre-annotating the next set of report texts using the trained small model and large model at the same time, wherein the quantity of any next set of report texts is greater than the quantity of previous set of report texts; and executing step M2 in a loop until the trained small model becomes an annotation model.

In an embodiment of the present invention, the step S1 specifically comprises:

step S11, pre-processing the report text to organize the report text into a recognizable report text;

step S12, parsing the recognizable report text, and recognizing each named entity classification label in the report text according to the named entity division rules;

step S13, traversing the recognizable report text, and annotating each named entity classification label and the text that is different from the named entity classification label using the BIO labeling method.

In an embodiment of the present invention, the step S11 "pre-processing the report text" specifically comprises:

searching the original report text based on pre-set rules, correcting misspellings, mixed Chinese and English characters, mixed upper- and lower-case characters, punctuation errors, abnormal numerical descriptions, irrelevant characters, and irregular descriptions in the original report text.

In an embodiment of the present invention, before the step S12, the method further comprises: establishing a named entity division rule;

the named entity division rule comprises:

establishing a corresponding relationship between the named entity classification label and the annotation information, the annotation information comprising: organ, description information corresponding to the organ, abnormal structure corresponding to the organ, description parameter corresponding to the abnormal structure, and time parameter identification.

In an embodiment of the present invention, the step S13 specifically comprises: annotating the initial character of each named entity classification label using a combination of a first prefix and annotation information, annotating the non-initial characters of each named entity classification label using a combination of a second prefix and annotation information, and annotating the text without annotation information with a third prefix, wherein the first prefix, the second prefix, and the third prefix are all different.

In an embodiment of the present invention, in the process of pre-annotating each set of report texts, the method further comprises:

segmenting each report text into multiple short sentences through punctuation, processing the same short sentences by deduplication and retaining one for pre-annotation, review and correction.

In order to solve one of the above-mentioned objects of the invention, an embodiment of the present invention provides an electronic device comprising a memory and a processor, the memory stores computer programs that can run on the processor, and the processor executes the computer programs to implement the steps of a method for structuring the capsule endoscopy report text described above.

In order to solve one of the above-mentioned objects of the invention, an embodiment of the present invention provides a computer-readable storage medium for storing computer programs, the computer programs can be executed by the processor to implement the steps of a method for structuring the capsule endoscopy report text described above.

Compared with the prior art, the beneficial effects of the present invention are: the method, device and medium for structuring capsule endoscopy report text of the present invention, can automatically annotate the capsule endoscopy report through the annotation model, and output parameters of different amount of information in different structures, and quantitative and accurate quality control of the capsule endoscopy process and examination results, which provide sufficient convenience for the electronic medical information of the capsule endoscopy.

BRIEF DESCRIPTION OF THE DRAWINGS

FIG. 5 is a schematic structural diagram of annotating report text using BIO labeling method in a specific example of the present invention;

FIG. 6 is a tree structure diagram formed by a specific example of the present invention;

FIG. 7 is an abnormal structure panel table formed by a specific example of the present invention;

FIG. 8 is a time parameter panel table formed by a specific example of the present invention.

DETAILED DESCRIPTION

The present invention can be described in detail below in conjunction with the specific embodiments shown in the accompanying drawings. However, the embodiments are not intended to limit the present invention, and the structural, method, or functional changes made by those skilled in the art in accordance with the embodiments are all included in the protection scope of the present invention.

Figure 1:
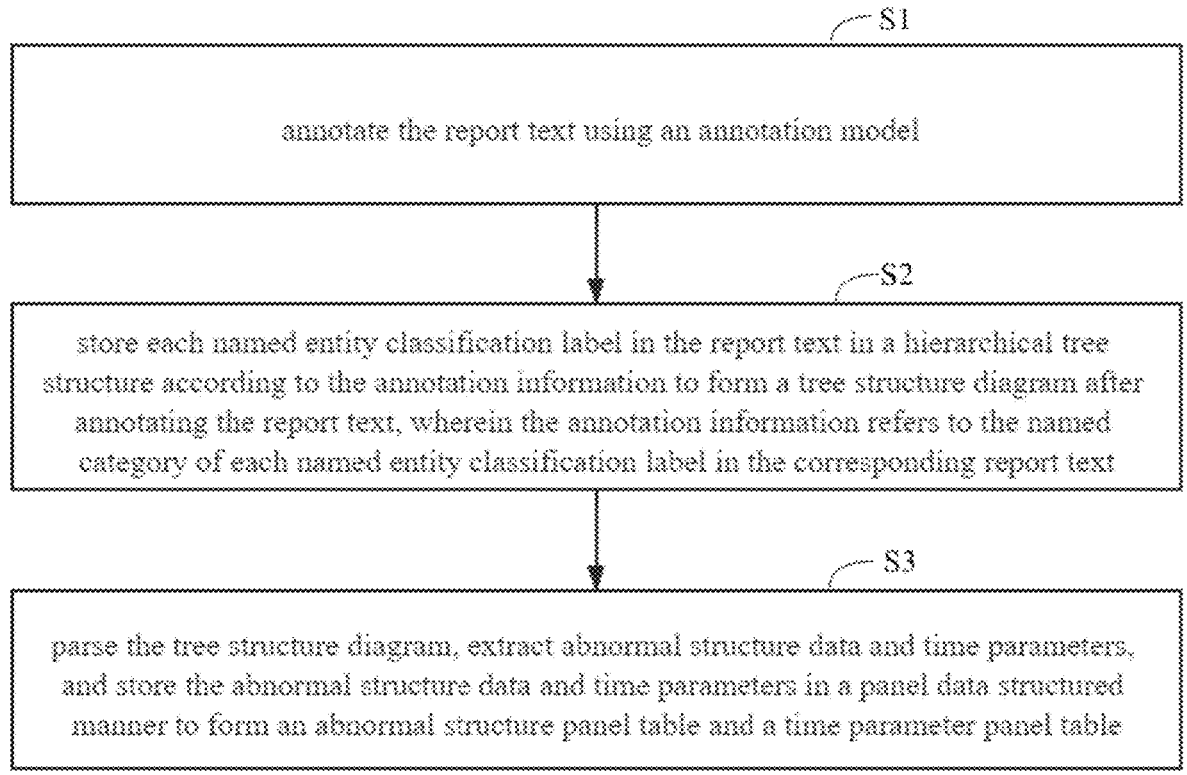
FIG. 1 is a schematic flowchart of a method for structuring a capsule endoscopy report text in accordance with an embodiment of the present invention.

As shown in FIG. 1, provided in the first embodiment of the present invention is a method for structuring a capsule endoscopy report text, the method comprises:

step S1, annotating the report text using an annotation model;

step S2, after annotating the report text, storing each named entity classification label in the report text in a hierarchical tree structure according to the annotation information to form a tree structure diagram; wherein the annotation information refers to the name category of each named entity classification label in the corresponding report text;

step S3, parsing the tree structure diagram, extracting abnormal structure data and time parameters, and storing the abnormal structure data and time parameters in a panel data structured manner to form an abnormal structure panel table and a time parameter panel table.

step S4, selectively outputting at least one of the tree structure diagrams, the abnormal structure panel table, and the time parameter panel table.

In an embodiment of the present invention, based on the consideration of model deployment performance, a small model of the BiLSTM+CRF structure is used to recognize the named entity of the report text; taking into account the accuracy of the model, a large model of BERT structure with higher accuracy is used to guide the training of the small model, and the accuracy of the BiLSTM+CRF small model is iteratively improved.

Figure 2:
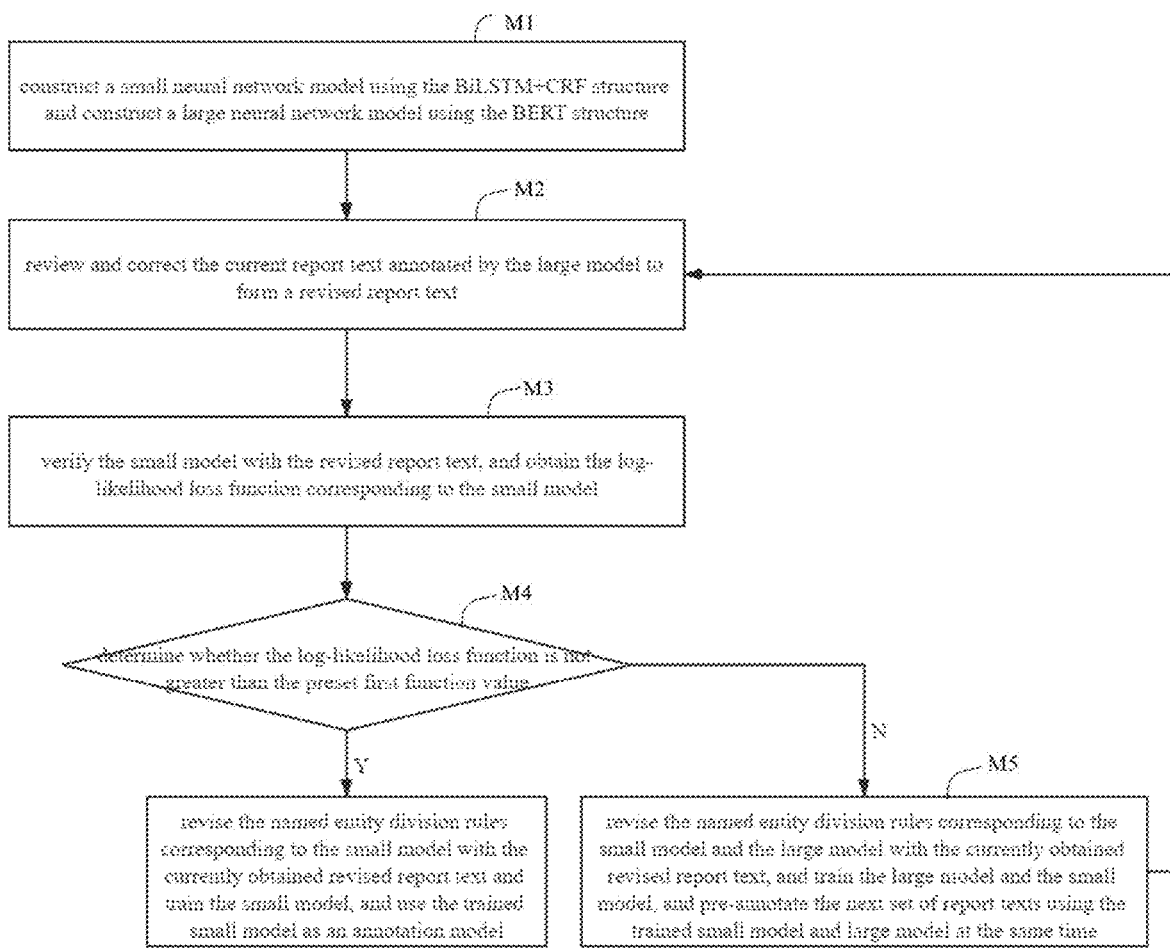
FIG. 2 is a schematic flowchart of a method for obtaining an annotation model in FIG. 1.

Specifically, as shown in FIG. 2, the method for obtaining the annotation model in step S1 specifically comprises: step M1, constructing a small neural network model using the BiLSTM+CRF structure and constructing a large neural network model using the BERT structure, wherein the initial small model and the large model have the same named entity division rules, and pre-annotating a current set of report texts using the small model and the large model, respectively;

step M2, reviewing and correcting the current report text annotated by the large model to form a revised report text;

step M3, verifying the small model with the revised report text, and obtaining the log-likelihood loss function corresponding to the small model;

step M4, revising the named entity division rules corresponding to the small model with the currently obtained revised report text and training the small model, and using the trained small model as an annotation model, when the log-likelihood loss function is not greater than the preset first function value; proceeding to step M5, when the log-likelihood loss function is greater than the preset first function value;

step M5, revising the named entity division rules corresponding to the small model and the large model with the currently obtained revised report text, and training the large model and the small model, and pre-annotating the next set of report texts using the trained small model and large model at the same time, wherein the quantity of any next set of report texts is greater than the quantity of previous set of report texts; and executing step M2 in a loop until the trained small model becomes an annotation model.

In the specific implementation process of the present invention, two deep learning neural network models of different scales, the BiLSTM+CRF and the BERT, based on the TensorFlow framework are used for the recognition of named entity classification labels.

The BiLSTM+CRF model is small, usually about 5-6 M, including a bidirectional LSTM layer and a conditional random field CRF layer. It can learn to obtain the contextual semantic information and the transition probability between words, constrain to make the named entity classification labels conform to legitimacy rules, and can predict entity types with high accuracy. After multiple rounds of iterative training, the accuracy of the validation set has been improved from an average of 90% to about 98%. In the preferred embodiment of the present invention, the small model BiLSTM+CRF undergoes multiple rounds of iterative training and knowledge transfer of the large model BERT, the training speed of the BiLSTM+CRF can be accelerated.

In the step M3, the BiLSTM+CRF model is optimized using the log-likelihood loss function, which can be expressed as: $L=-\Sigma_k \log(p(y_k|X))=-\Sigma_k \log(\text{softmax}(S(X, y_k)))$. Wherein, $p(y_k|X)$ is the maximum likelihood probability of the category vector X and the category logit vector $y_k$, wherein, the category vector X is the vector of the annotation information corresponding to the named entity classification label of the input report text, for example: the label of "gastric" in the named entity classification label "gastric fundus" is B-QG, corresponding to one-hot vector [1,0,0, . . . ], and the category logit vector $y_k$ is the output vector after the model recognizes the named entity, for example: the output unnormalized vector [1.35,0.23,−2.41, . . . ] of the model of "gastric" in the named entity classification label "gastric fundus".

$S(X, y_k)$ is the revised output score of the conditional random field, defined as:

$$S(X, y_k) = \sum_{i,k} v_k t_k(y_{i-1}, y_i, X, i) + \sum_{i,l} u_l s_l(y_i, X, i);$$

wherein, $t_k( \ldots )$ is the transfer characteristic function that depends on the current and previous position, $s_l( \ldots )$ is the state characteristic function that depends only on the current node position, $v_k$, $u_l$ are the corresponding weights, and the characteristic functions and weights are automatically learned by model training optimization.

Further, the BERT model is relatively large, of which the base model is about 400 M. It uses the Transformer module of bidirectional self-attention mechanism to improve expression ability. Based on the BERT Chinese pre-training model openly provided by Google and trained on a large number of Chinese corpora, the transfer fine-tuning training is performed on the report text data set, with a validation set accuracy of about 99% (compared with independent samples labeled by manual review). The BERT model is optimized using the cross-entropy loss function $L=-\Sigma_k q_k \log(P_k)$, wherein, $q_k$ is the one-hot vector of the named entity label category, for example: the label of "gastric" in "gastric fundus" is B-QG, corresponding to the one-hot vector [1, 0, 0, . . . ]; $P_k$ is the softmax normalized probability corresponding to the category vector output by the model recognition named entity, for example: the model output category normalization vector [0.92, 0.05, 0, . . . ] of "gastric" in "gastric fundus".

In a preferred embodiment of the present invention, the BERT model is also used for automatic pre-annotation in the iterative process to assist in training the BiLSTM+CRF model.

In the specific implementation process of the present invention, the automatic pre-annotation in the early stage depends on the matching of the named entity division rules preset in the model. The rule-based annotation has higher certainty and processing speed. However, the generalization ability of the rule-based annotation is slightly poor, there may be partial overlaps and conflicts between independent rules. Through multiple rounds of iterations to gradually update and improve the rules, the weaknesses of rule-based annotation can be effectively reduced.

Further, in the process of pre-annotating each set of report texts, the method further comprises: segmenting each report text into multiple short sentences through punctuation, processing the same short sentences by deduplication and retaining one for pre-annotation, review and correction.

Accordingly, the format and term descriptions of the report text obtained after capsule endoscopy are relatively fixed, and the report texts of different cases may have a plurality of identical descriptive short sentences. Perform deduplication of short sentences for the original report and record the identification ID and position information of each short sentence in the original report text, which is convenient for correct backfilling after the short sentence is annotated. After deduplication, pre-annotation and manual review by doctor can effectively reduce about 75% workload of repeated annotation, and can effectively avoid the inconsistency in annotation of the same short sentences in the original report text, which may affect the effect of subsequent model learning. After pre-annotation, review and correction, the short sentences with correct annotation information are backfilled into the original report text according to the position information stored in advance, so as to realize the complete annotation of the original report text.

Figure 3:
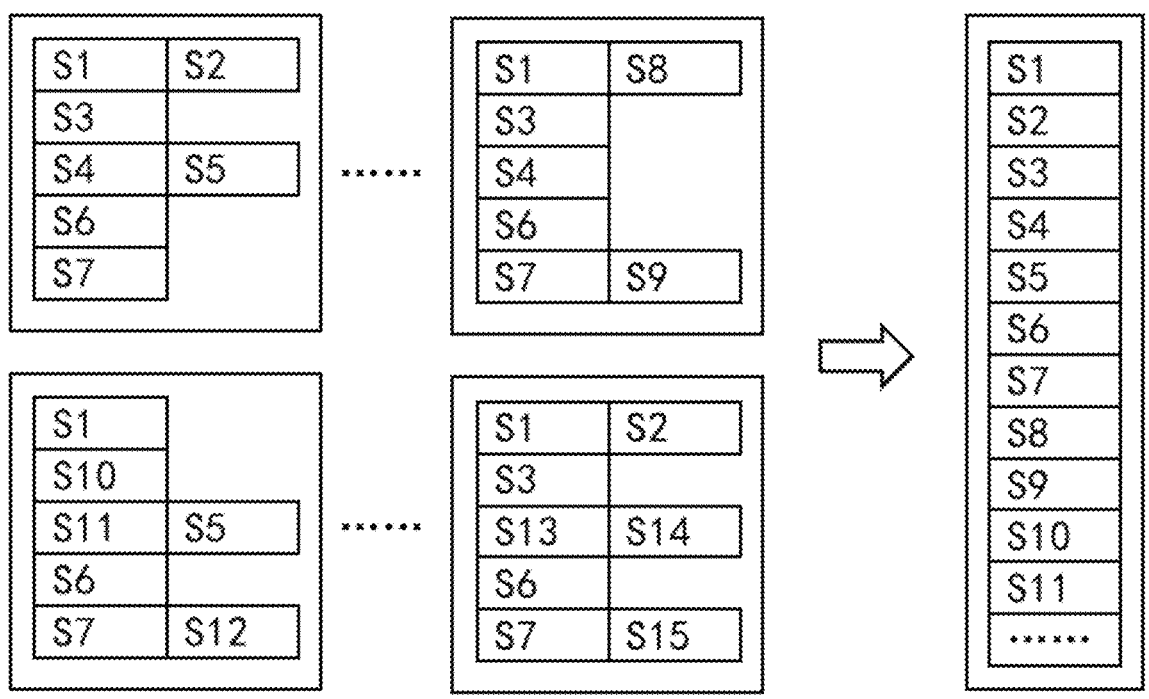
FIG. 3 is a schematic structural diagram of short sentences deduplication in a specific example of the present invention.

As shown in FIG. 3, in an example of the present invention, the texts at the left side of the arrow are unannotated, and S1 to S15 are multiple short sentences formed after segmentation. After deduplication, a set of short sentences, right side of the arrow, is formed.

Pre-annotation can recognize the named entity classification label with a higher accuracy, and automatic annotation on the report text using the annotation model can save about 95% of the manual annotation workload. With the iteration and upgrade of the named entity division rules and models, the accuracy of automatic pre-annotation can reach more than 98%. In addition, automatic pre-annotation using named entity division rules and models can ensure the consistency of a large number of text annotations and effectively avoid the individual difference and style drift faced by manual annotation of large amount of text data.

In the process of obtaining the above-mentioned annotation model, manual assistance is provided in reviewing the pre-annotated report text and correcting errors and annotating omissions. Manual review and correction can effectively improve the data set annotation quality and facilitate the iteration and upgrade of model learning training.

The deep learning neural network model is trained based on the reviewed report text. Since the deep learning neural network model has good reasoning performance and generalization ability in the field of natural language processing, it can achieve the accuracy of close to professional manual annotation in the task of named entity classification label recognition. Using a large number of well-annotated report texts for deep learning training and validation can obtain a neural network model with high accuracy and robustness. Automatically annotating the report text through the trained model can effectively improve the text structure consistency, automation and efficiency of implementation.

In a specific example of the present invention, multiple rounds of iteration are used to gradually establish and improve the named entity division rules of the report text. After 4 rounds of iterations, 24, 2059, 4950, and 4539 capsule endoscopy reports from actual cases are annotated in batches. Automatic pre-annotation based on rules and models can significantly reduce the cost of repeated manual annotation. In a preferred embodiment of the present invention, the report text is also reviewed and corrected by manual assistance, and the review and correction are used to train deep learning neural network model to facilitate annotating the new report text after model deployment. Through multiple rounds of iterative validation, the named entity division rules for annotation are gradually improved, and the neural network model is optimized. The model can achieve annotation of the report text with a high accuracy rate to ensure the quality of subsequent text structuring results.

It can be understood that, in actual project deployment, depending on the difference in equipment computing power and usage, one can choose to use deep learning neural network models of different orders of magnitude for named entity classification label recognition. The model (BiLSTM+CRF) of small order of magnitude can be deployed on CPU and can be applied to the online structuring of report text and report quality control; the model (BERT) of large order of magnitude can perform online tasks with GPU support, and can also batch-structure the massive collection of archived reports with a high accuracy rate, archive the structured results and build a knowledge graph.

Figure 4:
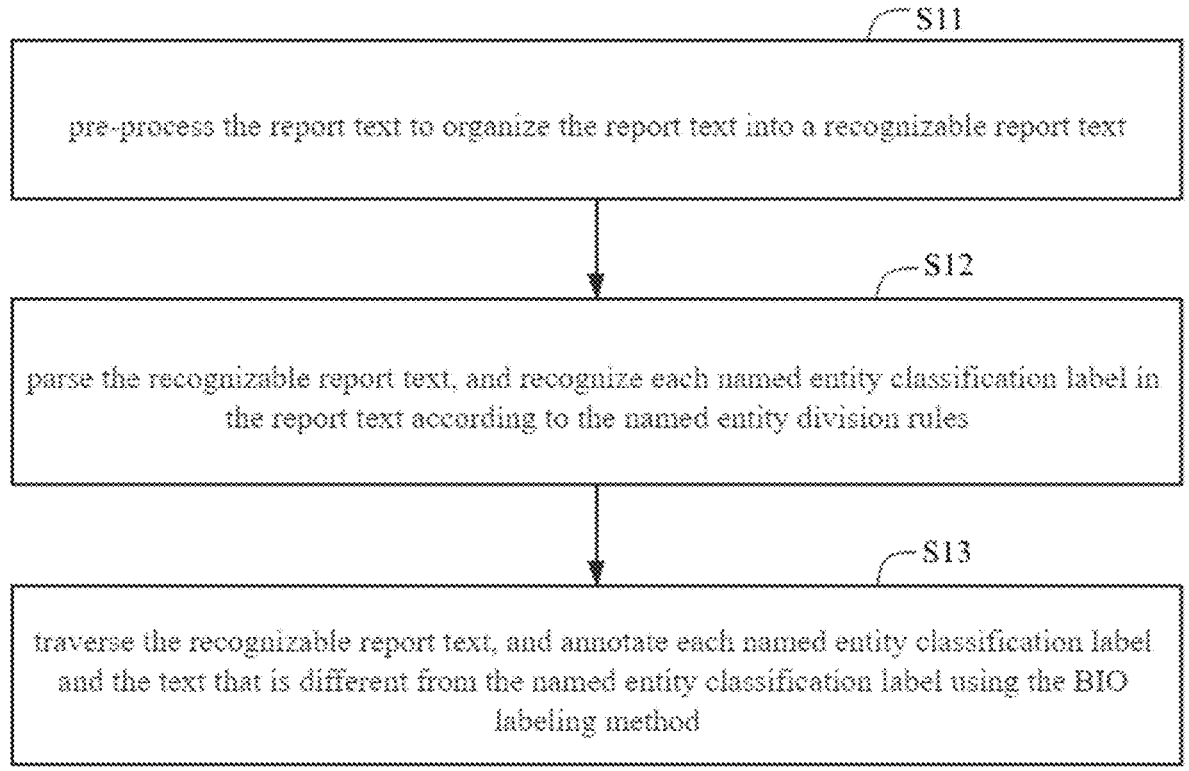
FIG. 4 is a schematic flowchart of a specific implementation process of step S1 in FIG. 1.

In the specific implementation process of the present invention, as shown in FIG. 4, the step S1 specifically comprises: step S11, pre-processing the report text to organize the report text into a recognizable report text;

step S12, parsing the recognizable report text, and recognizing each named entity classification label in the report text according to the named entity division rules;

step S13, traversing the recognizable report text, and annotating each named entity classification label and the text that is different from the named entity classification label using the BIO labeling method.

In an embodiment of the present invention, the step S11 "pre-processing the report text" specifically comprises: searching the original report text based on pre-set rules, correcting misspellings, mixed Chinese and English characters, mixed upper and lower case characters, punctuation errors, abnormal numerical descriptions, irrelevant characters, and irregular descriptions, etc. in the original report text, to effectively correct low-level errors in the original report text, and improve the quality of the report text and the quality of subsequent structured results. For example: through rule matching, correct "Zou Bi" (pinyin of Chinese) to "Zhou Bi" (pinyin of Chinese) and "0○ 4 cm" to "0.4 cm", correct "1 hour 2345" to "1 hour 23 minutes 45 seconds and so on". In the embodiments of the present invention, in the initial state, a set of rules can be set in advance. With the iterative learning of the report text, the rules can also change, so no further details are given here.

Before the step S12, the method further comprises: establishing a named entity division rule.

The named entity division rule comprises: establishing a corresponding relationship between the named entity classification label and the annotation information. The annotation information includes: organ, description information corresponding to the organ, abnormal structure corresponding to the organ, description parameter corresponding to the abnormal structure, and time parameter identification. Any annotation information corresponds to multiple named entity classification labels.

In the embodiments of the present invention, the annotation information may also include organization, attributes, performance, measured values, negative and error text, etc.; the annotation can be increased, decreased and modified with the category of each named entity classification label in the report text.

It should be noted that the report text obtained by capsule endoscopy is usually divided into several blocks, each of which has a different description. Thus, in the embodiments of the present invention, a named entity division rule corresponding to each block can be established, while for each block, perform the above steps synchronously or asynchronously, and output accordingly according to specific needs. For example, the report obtained by capsule endoscopy is usually divided into: examination findings, examination results, examination recommendations and other description blocks. In practical applications, each block can be structured separately.

In a specific example of the present invention, according to the statistical characteristics of the report text, the named entity classification label is matched with the annotation information to form a named entity division rule. Specifically, the organs include primary organs and secondary organs which have a superior-subordinate relationship.

Named entity classification labels corresponding to the primary organs include: oral cavity, esophagus, stomach, duodenum, small intestine, and large intestine. The secondary organs are further subdivisions of primary organs. The named entity classification labels corresponding to the secondary organs of stomach include: gastric fundus, cardia, gastric body, angulus, antrum, pylorus, etc. The named entity classification labels corresponding to the secondary organs of the duodenum include: bulb, descending part, horizontal part, ascending part, etc. The named entity classification labels corresponding to the secondary organs of the small intestine include: jejunum, ileum, etc. The named entity classification labels corresponding to the secondary organs of the large intestine include: cecum, appendix, colon, rectum, anal canal, etc. The named entity classification labels corresponding to the description information of the organs includes: dentate line, mucous lake, mucous membrane, blood vessel, lymphatic vessel, fold, epithelium, bulb cavity, intestinal cavity, intestinal wall, villi, etc. The named entity classification labels corresponding to abnormal structure of the organs include: polyps, bumps, ulcers, hyperplasia, erosions, hyperemia, bleeding, edema, redness, tumors, angiotelectasis, protrusions, depressions, lesions, tumors, inflammations, deformities, nodules, diverticula, niches, parasites, varicose veins, abnormal new organisms, etc. The named entity classification labels corresponding to the description parameters of the abnormal structure, such as the size of an abnormal structure, which may have multiple expressions, including but not limited to: number+Chinese (3.5* 4.5haomi (pinyin of Chinese), 0.8gongfen (pinyin of Chinese)), number+English (3.5*4.5 mm) and other types and their variants.

When the annotation type is a time parameter annotation, it involves a plurality of types, such as: total capsule running time, organ entry time, intra-organ running time, time of abnormal structure seen, etc. For each type, the corresponding named entity classification label has a variety of expressions, including but not limited to: numeric time (01:23:45), numeric Chinese time (1xiaoshi (pinyin of Chinese) 23fen (pinyin of Chinese) 45miao (pinyin of Chinese)), numeric English time (1 h23 min45 s) and their variants.

In the embodiments of the present invention, each named entity classification label and the text that is different from the named entity classification label are annotated using the BIO labeling method, so that it is convenient to accurately locate the named entity classification label according to the annotation processing result, and avoid confusion with adjacent similar entities. Specifically, the step S13 specifically comprises: annotating the initial character of each named entity classification label using a combination of a first prefix and annotation information, annotating the non-initial characters of each named entity classification label using a combination of a second prefix and annotation information, and annotating the text without annotation information with a third prefix, wherein the first prefix, the second prefix, and the third prefix are all different.

As shown in FIG. 5, in a specific example of the present invention, the annotation information is specifically divided into: organs, tissues, abnormal structures, attributes, performance, measured values, time, negation, and others, and each annotation information is identified with letters, which are: QG for organs, ZZ for tissues, YCJG for abnormal structures, SX for attributes, BX for performance, CLZ for measured values, SJ for time, FD for negation, and None for others.

Take the first named entity classification label "gastric fundus" obtained after searching as an example: the annotation information corresponding to "gastric fundus" is organ, wherein, "gastric" is the initial character, which is annotated with "B-QG", "fundus" is non-initial character, which is annotated with "I-QG," and ":" is a punctuation mark, not a named entity classification label, which is, in this example, annotated with "None".

As shown in FIG. 6, for step S2, the annotation information is divided into superior set relationships or named entity classification labels with corresponding relationships, which are stored in a hierarchical tree structure method to form a tree structure diagram during the storing and outputting, so as to effectively save data storage space and improve the efficiency of data retrieval and extraction. In the example shown in FIG. 6, the tree structure diagram classifies the annotation information, in which the primary organs, secondary organs, tissues and abnormal structures are gradually graded, and the cotyledon part stores descriptive text such as attributes and performance.

Further, for step S3, as shown in FIG. 7, special attention should be paid to the abnormal structures with suspected positive results, and panel data structuring is used for the location (primary organ, secondary organ) and size (description parameters of the abnormal structure) of the abnormal structure. It is convenient for relevant personnel to search and view target information more intuitively.

As shown in FIG. 8, in this example, the time parameters in the report text of the capsule endoscopy include: total running time of the capsule, part (organ), entry time (organ entry time), running time (intra-organ running time). These time parameters may be used for quality control, image rapid positioning, specific image extraction, etc. Panel data structuring is used to establish time value-related structuring, so that relevant personnel can search and view target information more intuitively.

For step S4, after the report text described in natural language is structured, the named entity classification labels in the report text are segmented with higher accuracy, and a clearer logical association is established between the named entity classification labels. In practical applications, it involves obtaining specific target information from a large amount of report text, such as: statistics related to abnormal structures and statistics of time parameters, etc. The examples shown in FIGS. 7 and 8 above are typical examples of target information extraction.

In addition, it should be noted that the target information involved in other tasks can be extracted from the tree structured diagram that establishes logical associations in a similar manner.

Preferably, the present invention provides an electronic device comprising a memory and a processor. The memory stores computer programs that can run on the processor, and the processor executes the computer programs to implement the steps of the method for structuring the capsule endoscopy report text described above.

Preferably, the present invention provides a computer-readable storage medium for storing computer programs. The computer programs can be executed by the processor to implement the steps of the method for structuring the capsule endoscopy report text described above.

Those skilled in the art can clearly understand that, for the convenience and conciseness purposes, the specific working process of the electronic device and storable medium thereof described above can refer to the corresponding process in the foregoing method implementation, which may not be repeated.

In summary, the method, device and medium for structuring capsule endoscopy report text of the present invention, can automatically annotate the capsule endoscopy report through the annotation model, and output parameters of different amount of information in different structures, and quantitative and accurate quality control of the capsule endoscopy process and examination results, which provide sufficient convenience for the electronic medical information of the capsule endoscopy.

It should be understood that, although the specification is described in terms of embodiments, not every embodiment merely comprises an independent technical solution. This narration in the specification is only for clarity. Those skilled in the art should have the specification as a whole, and the technical solutions in each embodiment may also be combined as appropriate to form other embodiments that can be understood by those skilled in the art.

The series of detailed descriptions listed above are only specific descriptions of the feasible embodiments of the present invention, and are not intended to limit the protection scope of the present invention. Any equivalent embodiments or variations made without departing from the technical spirit of the present invention should be included in the protection scope of the present invention.

What is claimed is:

1. A method for structuring a capsule endoscopy report text, comprising:
   annotating the report text using an annotation model;
   storing each named entity classification label in the report text in a hierarchical tree structure according to the annotation information to form a tree structure diagram wherein the annotation information refers to the named category of each named entity classification label in the corresponding report text;
   parsing the tree structure diagram, extracting abnormal structure data and time parameters;
   storing the abnormal structure data and time parameters in a panel data structured manner to form an abnormal structure panel table and a time parameters panel table;
   wherein obtaining the annotation model specifically comprises:
   step M1, constructing a small neural network model using the BiLSTM+CRF structure and constructing a large neural network model using the BERT structure, wherein the initial small model and the large model have the same named entity division rules, and pre-annotating a current set of report texts using the small model and the large model, respectively step M2, reviewing and correcting the current report text annotated by the large model to form a revised report text;

step M3, verifying the small model with the revised report text, and obtaining the log-likelihood loss function corresponding to the small model;

step M4, revising the named entity division rules corresponding to the small model with the currently obtained revised report text and training the small model, and using the trained small model as an annotation model, when the log-likelihood loss function is not greater than the preset first function value; proceeding to step M5, when the log-likelihood loss function is greater than the preset first function value;

step M5, revising the named entity division rules corresponding to the small model and the large model with the currently obtained revised report text, and training the large model and the small model, and pre-annotating the next set of report texts using the trained small model and large model at the same time, wherein the quantity of any next set of report texts is greater than the quantity of previous set of report texts; and executing step M2 in a loop until the trained small model becomes an annotation model.

2. The method of claim 1, wherein the method comprises : selectively outputting at least one of the tree structure diagram, the abnormal structure panel table, and the time parameter panel table.

3. The method of claim 1, wherein the step "annotating the report text using an annotation model" specifically comprises:
pre-processing the report text to organize the report text into a recognizable report text;
parsing the recognizable report text, and recognizing each named entity classification label in the report text according to the named entity division rules;
traversing the recognizable report text, and annotating each named entity classification label and the text that is different from the named entity classification label using the BIO labeling method.

4. The method of claim 3, wherein the step "pre-processing the report text" specifically comprises:
searching the original report text based on pre-set rules, correcting misspellings, mixed Chinese and English characters, mixed upper and lower case characters, punctuation errors, abnormal numerical descriptions, irrelevant characters, and irregular descriptions in the original report text.

5. The method of claim 3, wherein before the step "parsing the recognizable report text, and recognizing each named entity classification label in the report text according to the named entity division rules", the method further comprises:
establishing a named entity division rule,
wherein the named entity division rule comprises:
establishing a corresponding relationship between the named entity classification label and the annotation information, the annotation information comprising: organ, description information corresponding to the organ, abnormal structure corresponding to the organ, description parameter corresponding to the abnormal structure, and time parameter identification.

6. . The method of claim 3, wherein the step "traversing the recognizable report text, and annotating each named entity classification label and the text that is different from the named entity classification label using the BIO labeling method" specifically comprises:
annotating the initial character of each named entity classification label using a combination of a first prefix and annotation information, annotating the non-initial characters of each named entity classification label using a combination of a second prefix and annotation information, and annotating the text without annotation information with a third prefix, wherein the first prefix, the second prefix, and the third prefix are all different.

7. The method of claim 1, wherein in the process of pre-annotating each set of report texts, the method further comprises: segmenting each report text into multiple short sentences through punctuation, processing the same short sentences by deduplication and retaining one for pre-annotation, review and correction.

8. An electronic device, comprising a memory and a processor, wherein the memory stores computer programs that can run on the processor,
and the processor executes the computer programs to implement the steps of a method for structuring a capsule endoscopy report text,
wherein the method comprises:
annotating the report text using an annotation model;
storing each named entity classification label in the report text in a hierarchical tree structure according to the annotation information to form a tree structure diagram, wherein the annotation information refers to the named category of each named entity classification label in the corresponding report text;
parsing the tree structure diagram, extracting abnormal structure data and time parameters, and storing the abnormal structure data and time parameters in a panel data structured manner to form an abnormal structure panel table and a time parameters panel table;
wherein obtaining the annotation model specifically comprises:
step M1, constructing a small neural network model using the BiLSTM+CRF structure and constructing a large neural network model using the BERT structure, wherein the initial small model and the large model have the same named entity division rules, and pre-annotating a current set of report texts using the small model and the large model, respectively
step M2, reviewing and correcting the current report text annotated by the large model to form a revised report text;
step M3, verifying the small model with the revised report text, and obtaining the log-likelihood loss function corresponding to the small model;
step M4, revising the named entity division rules corresponding to the small model with the currently obtained revised report text and training the small model, and using the trained small model as an annotation model, when the log-likelihood loss function is not greater than the preset first function value; proceeding to step M5, when the log-likelihood loss function is greater than the preset first function value;
step M5, revising the named entity division rules corresponding to the small model and the large model with the currently obtained revised report text, and training the large model and the small model, and pre-annotating the next set of report texts using the trained small model and large model at the same time, wherein the quantity of any next set of report texts is greater than the quantity of previous set of report texts; and executing step M2 in a loop until the trained small model becomes an annotation model.

9. A computer-readable storage medium storing computer programs,
wherein the computer programs can be executed by the processor to implement the steps of a method for structuring a capsule endoscopy report text,
wherein the method comprises:
annotating the report text using an annotation model;
storing each named entity classification label in the report text in a hierarchical tree structure according to the annotation information to form a tree structure diagram, wherein the annotation information refers to the named category of each named entity classification label in the corresponding report text;
parsing the tree structure diagram, extracting abnormal structure data and time parameters, and storing the abnormal structure data and time parameters in a panel data structured manner to form an abnormal structure panel table and a time parameters panel table. wherein obtaining the annotation model specifically comprises:
step M1, constructing a small neural network model using the BiLSTM+CRF structure and constructing a large neural network model using the BERT structure, wherein the initial small model and the large model have the same named entity division rules, and pre-annotating a current set of report texts using the small model and the large model, respectively
step M2, reviewing and correcting the current report text annotated by the large model to form a revised report text;
step M3, verifying the small model with the revised report text, and obtaining the log-likelihood loss function corresponding to the small model;
step M4, revising the named entity division rules corresponding to the small model with the currently obtained revised report text and training the small model, and using the trained small model as an annotation model, when the log-likelihood loss function is not greater than the preset first function value; proceeding to step M5, when the log-likelihood loss function is greater than the preset first function value;
step M5, revising the named entity division rules corresponding to the small model and the large model with the currently obtained revised report text, and training the large model and the small model, and pre-annotating the next set of report texts using the trained small model and large model at the same time, wherein the quantity of any next set of report texts is greater than the quantity of previous set of report texts; and executing step M2 in a loop until the trained small model becomes an annotation model.

* * * * *